US005755714A

United States Patent [19]

Murphy-Chutorian

[11] Patent Number: 5,755,714
[45] Date of Patent: May 26, 1998

[54] SHAPED CATHETER FOR TRANSMYOCARDIAL REVASCULARIZATION

[75] Inventor: Douglas R. Murphy-Chutorian, Sunnyvale, Calif.

[73] Assignee: Eclipse Surgical Technologies, Inc., Sunnyvale, Calif.

[21] Appl. No.: 714,893

[22] Filed: Sep. 17, 1996

[51] Int. Cl.$^6$ ...................................... A61B 17/36
[52] U.S. Cl. ........................ 606/15; 606/7; 607/89; 607/122
[58] Field of Search ..................... 606/7, 13-16; 607/122, 89; 604/22, 280, 281

[56] References Cited

U.S. PATENT DOCUMENTS

| | | | |
|---|---|---|---|
| 4,658,817 | 4/1987 | Hardy. | |
| 4,669,465 | 6/1987 | Moore et al.. | |
| 4,846,171 | 7/1989 | Kaupusman. | |
| 5,104,393 | 4/1992 | Isner et al. | 606/15 |
| 5,114,403 | 5/1992 | Clarke et al. | 604/96 |
| 5,125,926 | 6/1992 | Rudko et al. | 606/19 |
| 5,255,679 | 10/1993 | Imran | 128/642 |
| 5,304,139 | 4/1994 | Adams et al. | 607/122 |
| 5,380,316 | 1/1995 | Aita e tal. | 606/7 |
| 5,389,096 | 2/1995 | Aita et al. | 606/15 |
| 5,465,717 | 11/1995 | Imran et al. | 128/642 |
| 5,575,785 | 11/1996 | Abela et al. | 606/15 |
| 5,607,462 | 3/1997 | Imran | 607/122 |
| 5,643,253 | 7/1997 | Baxter et al. | 606/15 |

FOREIGN PATENT DOCUMENTS 0515 867 A2  12/1992  European Pat. Off..

OTHER PUBLICATIONS

Deckelbaum, "Cardiovascular Apps. of Laser Tech.", Lasers in Surgery and Medicine, 15:315–341 (1994).
Frazier et al., "Myocard. Revasc. with Las.", Cullen Cardio. Res. Labs., Tx. Heart Inst., Supp. II C vol. 92, No. 9, II-58-65 (Nov. 1, 1995).

*Primary Examiner*—Ruth S. Smith
*Attorney, Agent, or Firm*—Ray K. Shahani; Janet Kaiser Castaneda; Christopher N. Sears

[57] ABSTRACT

A shaped catheter for accessing and treating preselected surfaces of cavities and organs within the human body, the apparatus including a tubular, shaped outer sheath with at least one guide hole and a tubular, flexible inner sleeve with a distal opening disposed adjacent the distal end, the inner sleeve slidably disposed within the outer sheath such that the distal opening of the inner sleeve can be operatively positioned adjacent the at least one of the guide holes and a laser delivery device or other functional device can be extended through the distal opening of the inner sleeve and through the guide hole on the outer sheath into the body cavity or organ. Providing a plurality of guide holes on the outer sheath will allow sequential treatment of the preselected surface within the body cavity or organ. Multiple TMR channels can be created or treatment at a number of sites can be made without moving or otherwise repositioning the outer sheath. The invention is also a method of use of such apparatus.

24 Claims, 4 Drawing Sheets

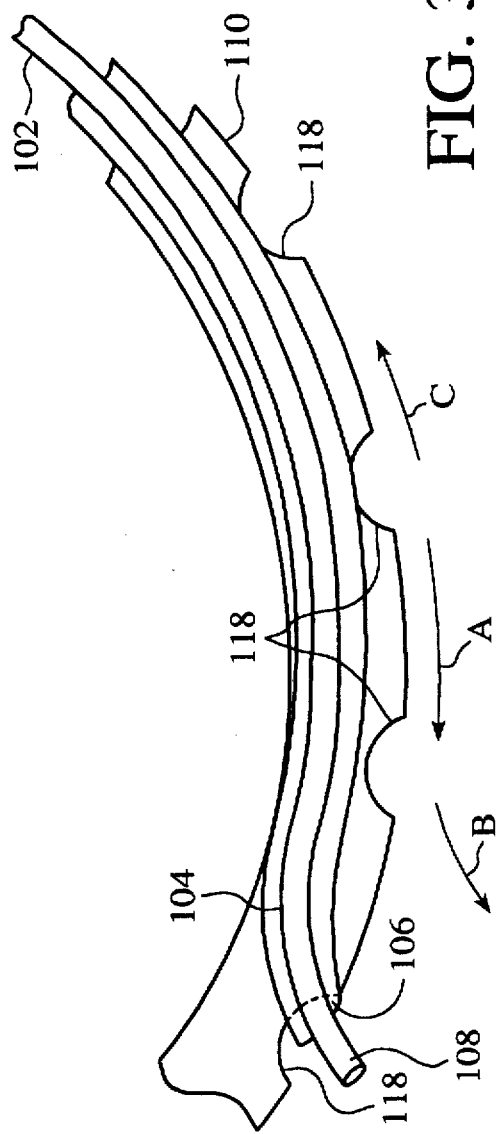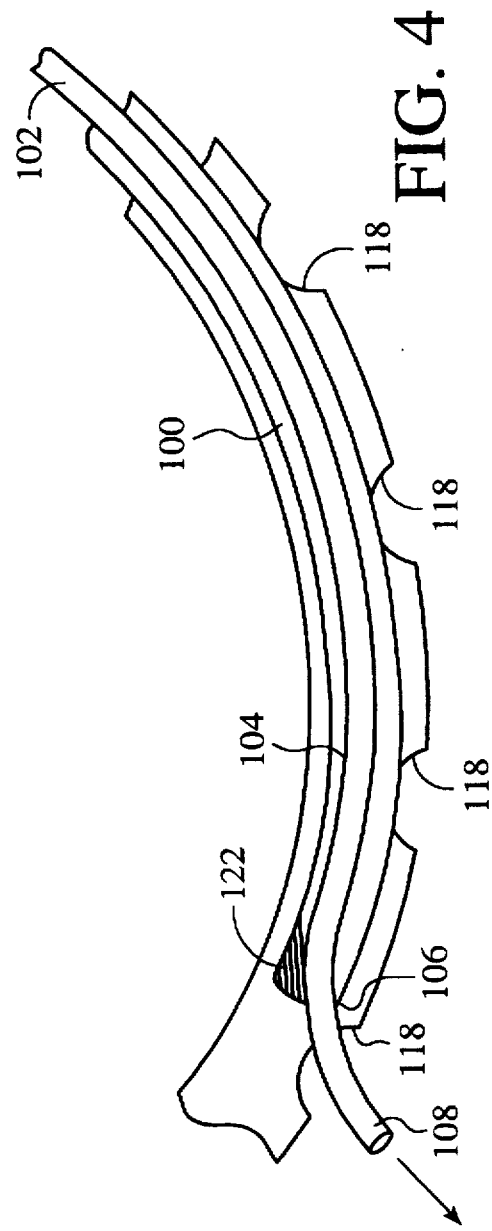

1

SHAPED CATHETER FOR TRANSMYOCARDIAL REVASCULARIZATION

FIELD OF THE INVENTION

The present invention relates generally to catheter procedures involving laser energy delivery using fiber optic and other laser delivery systems. More particularly, the invention relates to a shaped catheter apparatus having an outer sheath with a number of guide holes and an inner flexible sleeve for selectively directing the distal end of an optical fiber, other type of laser delivery means or other device through the holes on the outer sheath, particularly adapted for use in laser-assisted transmyocardial revascularization (TMR).

BACKGROUND OF THE INVENTION

In the treatment of heart disease, one method of improving myocardial blood supply is called transmyocardial revascularization (TMR), the creation of channels in the myocardium of the heart. The procedure using needles in a form of surgical "myocardial acupuncture" has been used clinically since the 1960s. Deckelbaum. L. I., Cardiovascular Applications of Laser technology, *Lasers in Surgery and Medicine* 15:315–341 (1994). The technique relieves ischemia by allowing blood to pass from the ventricle through the channels either directly into other vessels communicating with the channels or into myocardial sinusoids which connect to the myocardial microcirculation.

In the reptilian heart, perfusion occurs via communicating channels between the left ventricle and the coronary arteries. Frazier, O. H., Myocardial Revascularization with Laser—Preliminary Findings. *Circulation*, 1995; 92 [suppl II]:II-58–II-65. There is evidence of these communicating channels in the developing human embryo. In the human heart, myocardial microanatomy involves the presence of myocardial sinusoids. These sinusoidal communications vary in size and structure, but represent a network of direct arterial-luminal, arterial-arterial, arterial-venous, and venous-luminal connections. This vascular mesh forms an important source of myocardial blood supply in reptiles but its role in humans is poorly understood.

Numerous surgical TMR studies have been performed, including early studies using needles to perform myocardial acupuncture, or boring, to mechanically displace and/or remove tissue. Such studies have involved surgically exposing the heart and sequentially inserting needles to form a number of channels through the epicardium, myocardium, and endocardium to allow blood from the ventricle to perfuse the channels. The early studies using needles showed that the newly created channels were subject to acute thrombosis followed by organization and fibrosis of clots resulting in channel closure. Interest in TMR using needles waned with the knowledge that such channels did not remain open. However, interest in TMR procedures has recurred with the advent of medical lasers used to create TMR channels. Histological evidence of patent, endothelium-lined tracts within laser-created channels shows that the lumen of laser channels can become hemocompatible and resists occlusion. A thin zone of charring occurs on the periphery of the laser-created channels through the well-known thermal effects of optical radiation on cardiovascular tissue. Additionally, recent histological evidence shows probable new vessel formation adjacent collagen occluded transmyocardial channels, thereby suggesting benefits from TMR with or without the formation of channels which remain patent.

Surgical TMR procedures using laser energy have been described in the prior art. U.S. Pat. No. 4,658,817 issued Apr. 21, 1987 to Hardy teaches a method and apparatus for surgical TMR using a $CO_2$ laser connected to an articulated arm having a handpiece attached thereto. The handpiece emits laser energy from a single aperture and is moved around the surface of the heart to create the desired number of channels. U.S. Pat. No. 5,380,316 issued Jan. 10, 1995 to Aita et al. purports to teach the use of a flexible lasing apparatus which is inserted into the open chest cavity in a surgical procedure. A lens at the distal end of the flexible apparatus is used to focus laser energy, and the apparatus is moved about the surface of the heart to create the desired number of channels.

The foregoing discussion relates to surgical procedures, i.e. procedures which access the heart surgically, either via open heart surgery, or perhaps by minimally invasive surgical (MIS) methods if the design and size of the distal ends of the hand pieces are suitable for use in an MIS site. However, since TMR most often involves creating channels through the endothelium into the lower left chamber of the heart, it is desirable to create, TMR channels in a percutaneous procedure, i.e. by extending a catheter apparatus through the vasculature into the ventricle and creating the channels through endocardial surfaces and into myocardium. Performing such percutaneous TMR is desirable for a number of reasons. Percutaneous catheter procedures are typically less traumatic to the patient compared to surgical procedures. Adhesions between the pericardial sac and epicardium are eliminated. Percutaneous TMR with a catheter apparatus also officers an alternative solution to persons who are not candidates for surgical procedures.

Because TMR procedures generally involve creating a plurality of channels within the myocardium, performing the procedure percutaneously requires the ability to steer the catheter apparatus through the vasculature and maneuver the apparatus within the ventricle of the beating heart as rapidly as possible to create the channels without subjecting the heart to the undue stress of a lengthy procedure. Additionally, the ability to control and stabilize the catheter apparatus against the beating heart wall while creating channels with a laser is desirable for percutaneous procedures to ensure creation of channels as desired and to ensure that the laser is fired only within the myocardial tissue. TMR channels should be spaced and grouped appropriately to achieve the desired result without weakening or rupturing the heart muscle.

The early myocardial acupuncture procedures were not performed percutaneously. The Hardy $CO_2$ laser delivery system described above is rigid, relatively large, and not adaptable for percutaneous use. The Aita '316 patent does not suggest a method for percutaneous use of the single aperture, laser delivery device described therein for surgical use.

U.S. Pat. No. 5,389,096 issued Feb. 14, 1995 to Aita et al. purports to teach one method of percutaneous TMR using an elongated flexible lasing apparatus with control lines and a focusing lens structure at the distal tip. The method describes the use of pressure to attempt to stabilize the apparatus against the wall of the heart. The '096 apparatus requires movement and restabilization of the apparatus prior to the creation of each channel. Neither of these patents, nor any other prior art, describes or suggests creation of TMR channels quickly and grouping of channels appropriately.

Several prior art patents describe the use of catheters within the ventricle for percutaneous treatment of ventricular tachycardia. Such devices have a means to locate an arrhythmia site and ablate the site, at or just below the ventricle surface, using an electrode device or laser energy. U.S. Pat. No. 5,104,393 issued Apr. 14, 1992 to Isner teaches a catheter apparatus having a guiding Y-shaped sheath and guiding catheter assembly for introducing an optical fiber into the ventricle. Positioning is described to enable a single burst of laser energy from a single aperture to ablate the site. However, positioning or specific steering means sufficient to create one or more TMR channels is not described or suggested.

U.S. Pat. Nos. 5,255,679 issued Oct. 26, 1993 and 5,465, 717 issued Nov. 14, 1995 to, respectively, Imran and Imran et al., disclose non-laser, basket-shaped catheter apparatus for mapping and/or ablation of arrhythmia sites within the ventricle. A pull wire is used to expand the basket portion within the ventricle, and a plurality of electrodes on the arms of the basket are used for ablation. The basket device is designed to place the; electrodes on the ventricle wall. No provision is made for a laser delivery system, and no positioning means is provided to allow creation of TMR channels.

As can be seen from description of the prior art above, percutaneous TMR catheters are virtually unknown with the exception of the single aperture catheter briefly described in the '096 Aita patent. There is a need in the art for a percutaneous TMR catheter shaped to correspond to the contours of the ventricle, having means for positioning the catheter to the ventricle wall, and having multiple ports for a laser delivery means to enable rapid creation of a plurality of appropriately grouped and spaced TMR channels without repositioning the catheter.

SUMMARY OF THE INVENTION

Thus, it is an advantage of the present invention to provide a catheter apparatus and method of use for percutaneous TMR, or any stimulation procedure, which overcome the limitations of the prior art.

It is a further advantage of the present invention to provide a catheter apparatus capable of being guided into a heart chamber and used therein for creating a plurality of TMR channels controllably and efficiently.

It is a further advantage of the present invention to provide a j-shaped catheter with a sleeve.

It is a further advantage of the present invention to provide a catheter having an outer sheath and an inner sleeve to guide an optical fiber or other laser delivery means selectively through a number of positions to exit through apertures or guide holes in the outer sheath.

It is yet a further advantage of the present invention to provide a percutaneous catheter which can be positioned securely into a predetermined position within the ventricle.

A further advantage of the present invention is to provide an apparatus to enable creation of a plurality of appropriately grouped and spaced TMR channels on a preselected surface within a body cavity or organ quickly and safely and without repositioning the catheter.

A shaped catheter with sleeve apparatus for surgical and catheter procedures, particularly percutaneous TMR, is disclosed herein. The catheter apparatus is comprised essentially of an outer sheath having a generally j-shaped distal end, a flexible insert sleeve and at least one laser delivery means disposed within the inner sleeve. The outer sheath has a plurality of guide holes located at preselected positions on the outer sheath sidewall along the curvature and is designed to be placed inside a heart chamber. The corresponding inner sleeve is Manufactured to be somewhat more flexible than the outer sheath and has an opening at the distal end which will permit a laser delivery means such as an optical fiber to be extended through the distal end of the inner sleeve for exit through one of the plurality of guide holes on the outer sheath. The shaped curvature of the distal end of the outer sheath allows the distal end of the outer sheath with guide holes to be placed in contact with a curved surface structure for treatment thereon. Thus, with regard to TMR, a laser delivery means, such as an optical fiber or fiber bundle, can be advanced through the guide holes sequentially for creating a series of TMR channels.

Numerous other advantages and features of the present invention will become readily apparent from the following detailed description of the invention and the embodiments thereof, from the claims and from the accompanying drawings.

BRIEF DESCRIPTION OF THE DRAWINGS

FIG. 3 is a representative lengthwise cross sectional view of a preferred embodiment of both the inner sleeve and the outer sheath of the shaped catheter of the present invention, the inner sleeve having a curvature opposing that of the shaped outer sheath in a region adjacent its distal end of the inner sleeve.

FIG. 4 is a representative lengthwise cross sectional view of a preferred embodiment of both the inner sleeve and the outer sheath of the shaped catheter of the present invention, the inner sleeve having a cam member adjacent its distal end.

DETAILED DESCRIPTION OF THE PREFERRED EMBODIMENT

Figure 1:
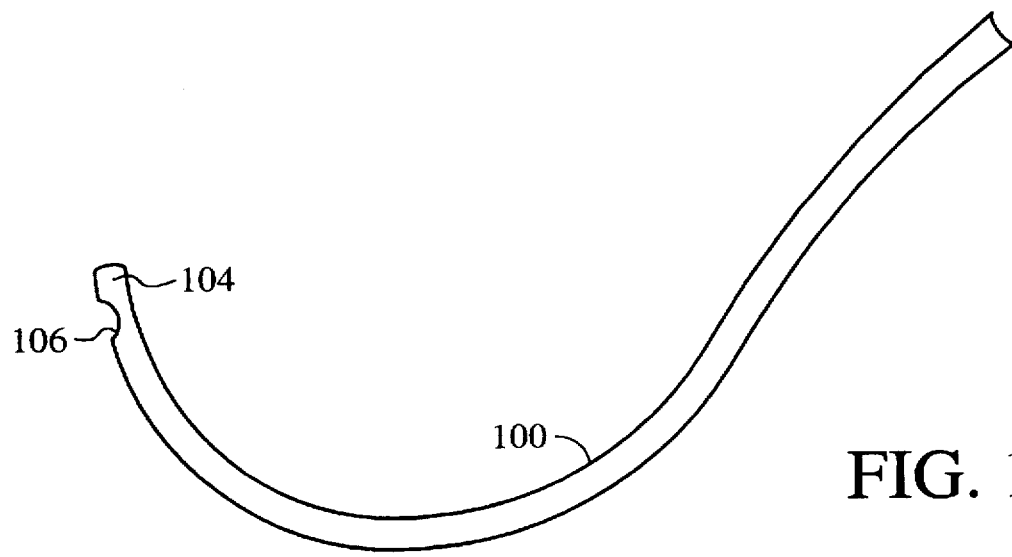
FIG. 1 is a representative lengthwise perspective view of a preferred embodiment of the inner sleeve of the shaped catheter of the present invention.

FIG. 1 is a representative lengthwise perspective view of a preferred embodiment of the inner sleeve of a shaped catheter of the present invention. An inner sleeve 100 is a hollow flexible insert. It can have a preformed curvature or can be essentially non-curved. An optical fiber 102, fiber bundle or other laser delivery means is inserted into the proximal end of the inner sleeve 100. The distal end 104 of the inner sleeve 100 has an opening 106 for selectively directing the distal end 108 of the laser delivery means 102 through a guide hole in an outer sheath.

The inner sleeve 106 of the apparatus is semi-flexible, but rigid enough to hold its shape and to be pushed or steered independently from the outer sheath. It is also flexible enough to be pushed and steered through bends and turns along desired paths within the body. For example, catheterization procedures often involve introducing such equipment to the human body via the femoral artery and advancing the equipment to the desired location through the vasculature. In TMR, application of laser energy to portions of endocardium from within the left ventricular chamber of the heart can be achieved, for example, by introducing the catheter to the left ventricle via the femoral artery, through the aorta and aortic arch and into the left ventricle.

Figure 2A:
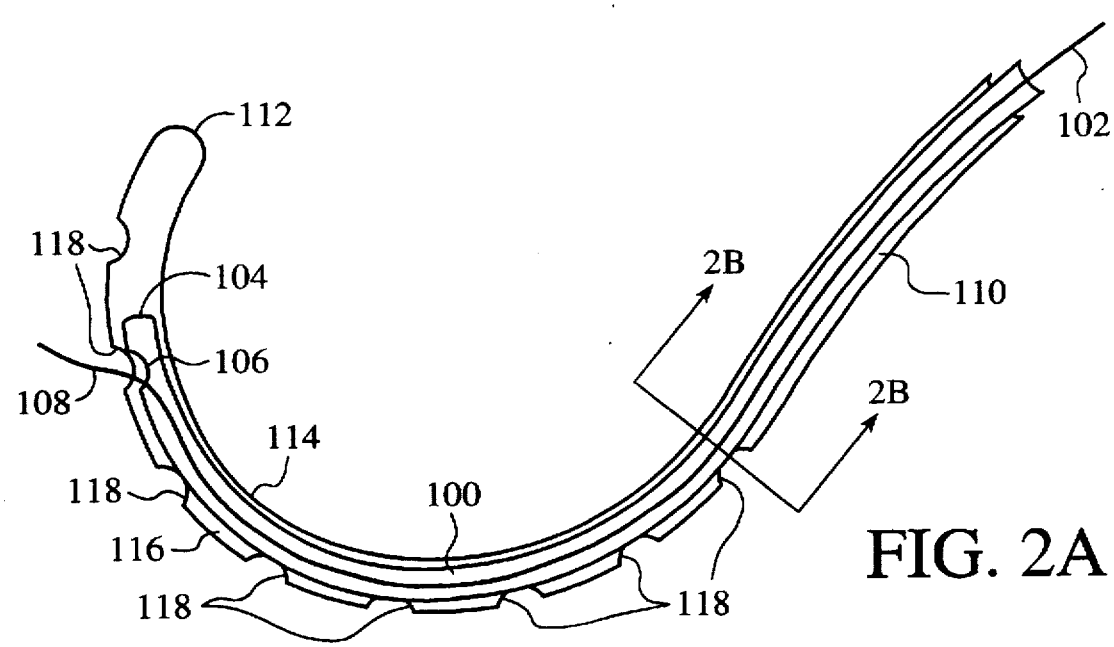
FIG. 2A is a representative lengthwise cross sectional view of a preferred embodiment of both the inner sleeve and the outer sheath of the shaped catheter of the present invention.

FIG. 2A is a representative lengthwise cross sectional view of a preferred embodiment of both the inner sleeve and the outer sheath of the shaped catheter of the present invention. As shown, the distal end 104 of the inner sleeve 100 can be positioned at least as far through the outer sheath 110 as the distal end 112 of the outer sheath 110. The outer sheath is semi-rigid and is generally curved to follow the shape of the region in which the apparatus is being used, for instance the wall of the ventricle. The curvature of the outer sheath defines an inner radial portion 114 and an outer radial portion 116. A number of guide holes 118 are arrayed on the outer sheath 110 along an outer radial portion 116. These guide holes 118 can also be placed on other portions of the outer sheath 110, such as on the inner radial portion 114 and between the inner and the outer radial portions.

The guide holes themselves must be formed in the outer sheath in such a way as to permit steerability of the laser delivery means therethrough. Typically, these guide holes will be elongated into an oval or ellipse shape. They will be smoothed, rounded or otherwise treated to facilitate and enhance the exit of the laser delivery optical fiber.

It will be clear that the inner sleeve 100 is slidable within the outer sheath 110. Therefore, as the inner sleeve is extended or retracted within the outer sheath 110 the opening 106 at the distal end 104 of the inner sleeve will be aligned with one of the plurality of guide holes 118 in the outer radial portion 116 of the sidewall of the outer sheath 110. Alignment will allow a laser delivery means 102 or other functional device to be extended through the inner sleeve and out an guide hole in the outer sheath to treat a preselected surface area or other structure.

In operation, once the outer sheath 110 is placed adjacent preselected surface areas or other structures for treatment, the inner sleeve 100 can be positioned operatively. A laser delivery means 102 or other functional device can be inserted through the inner sleeve and through a first guide hole 118 in the outer sheath. Once treatment has been completed with the laser delivery means, it can be retracted back into the inner sleeve. Thereafter, the inner sleeve can be repositioned so as to realign the opening at the distal end of the inner sleeve with a second one of the plurality of guide holes in the outer sheath. By extending the laser delivery means or other functional device therethrough, a second surface area or other preselected structure can be treated, visualized, etc. It will be apparent to those skilled in the art that by repeating this procedure a number of times, a number of surface areas or other preselected structures within an opening, body lumen or otherwise can be rapidly treated, visualized, etc. in a predetermined sequence.

Figure 2B:
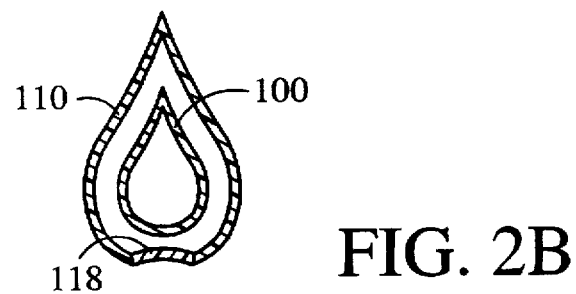
FIG. 2B is a representative cross sectional view of a preferred embodiment of both the inner sleeve and the outer sheath of the shaped catheter of the present invention taken across 2A.

FIG. 2B is a representative cross sectional view of a preferred embodiment of both the inner sleeve and the outer sheath of the shaped catheter of the present invention taken across 2A. Both the inner sleeve 100 as well as the outer sheath 110 have corresponding tear-shaped cross sectional areas. In this manner, the inner sleeve can be extended and retracted through the outer sheath with the inner sleeve maintaining a fixed axial orientation with respect to the outer sheath. This configuration will aid in controlling the inner sleeve. It will be clear hereby that the precise shape of the cross sectional areas of the inner sleeve and the outer sheath can be different, but as long as the shape of both cross sections match or key to each other the inner sleeve can be positioned precisely at a predetermined angular orientation within the outer sheath and maintained in that position during subsequent extension of a laser delivery means or other functional device through the inner sleeve and out one or more of the plurality of guide holes in the outer sheath.

It will be understood that depth stop means in a preferred embodiment consists of a small compression clamp or fiber advance mechanism which limits the distance the fiber may be advanced through the guide holes.

FIG. 3 is a representative lengthwise cross sectional view of a preferred embodiment of both the inner sleeve and the outer sheath of the shaped catheter of the present invention, the inner sleeve having a curvature opposing that of the outer sheath in a region adjacent the distal end of the inner sleeve. The outer sheath 110 has a distinct curvature with a direction of curvature represented by directional arrow A. It will be understood that the outer sheath and the inner sleeve together define a central axis which runs through the central hollow openings within the outer sheath and inner sleeve essentially parallel to directional arrow A through most of the assembly with the exception of those portions of the outer sheath and inner sleeve adjacent their distal ends. However, in this embodiment, the distal end 104 of the inner sleeve 100 also has a distinct, opposing curvature with its own direction of curvature represented by directional arrow B. This combination of operative curvatures will serve to precisely orient the opening 106 at the distal end of the inner sleeve 100 adjacent one or more of the guide holes 118 by physically matching end geometries. The distal opening 106 of the inner sleeve will lock or snap into a temporary groove or detent-type position as the inner sleeve is extended or retracted through the outer sheath. This curvature will also serve to deflect the distal end 108 of the laser delivery means 102 or other functional device out the opening at the distal end of the inner sleeve and through one or more of the guide holes of the outer sheath. Thus, as the inner sleeve is moved within the outer sheath, the opening in the distal end of the inner sleeve can be operatively positioned adjacent one or more of the guide holes sequentially or otherwise selectively. It will be understood that in a preferred embodiment, the distal end 104 of the inner sleeve 100 will be large enough not to pass through the plurality of guide holes 118 on the outer sheath 110. This will permit the inner sleeve 100 to be extended in the direction shown by directional arrow A as well as to be retracted in an opposite direction shown by directional arrow C so as to allow the selective and/or sequential extension of the laser delivery means 102 or other functional device through one or more of the guide holes 118.

FIG. 4 is a representative lengthwise cross sectional view of a preferred embodiment of both the inner sleeve and the outer sheath of the shaped catheter of the present invention, the inner sleeve having a cam member 122 at its distal end. The cam member 122 is located adjacent the opening 106 in the distal end 104 of the inner sleeve 100. This cam member comprises a groove, ramp or swell which deflects the laser delivery means 102 or other functional device in a direction represented by the directional arrow. In this embodiment, the inner sleeve 100 is free to slide within the outer sheath. Its distal end 104 can be positioned operatively adjacent one or more of the plurality of guide holes 118 of the outer sheath. This curvature imparted by the cam member 122 will also serve to deflect the distal end 108 of the optical fiber 102 or other laser delivery means or functional device out the opening at the distal end of the inner sleeve and through one or more of the guide holes of the outer sheath. Thus, as the inner sleeve is moved within the outer sheath, the opening in the distal end of the inner sleeve can be operatively positioned adjacent one or more of the guide holes so as to allow the selective and/or sequential extension of the laser delivery means 102 or other functional device through one or more of the guide holes 118.

Figure 5:
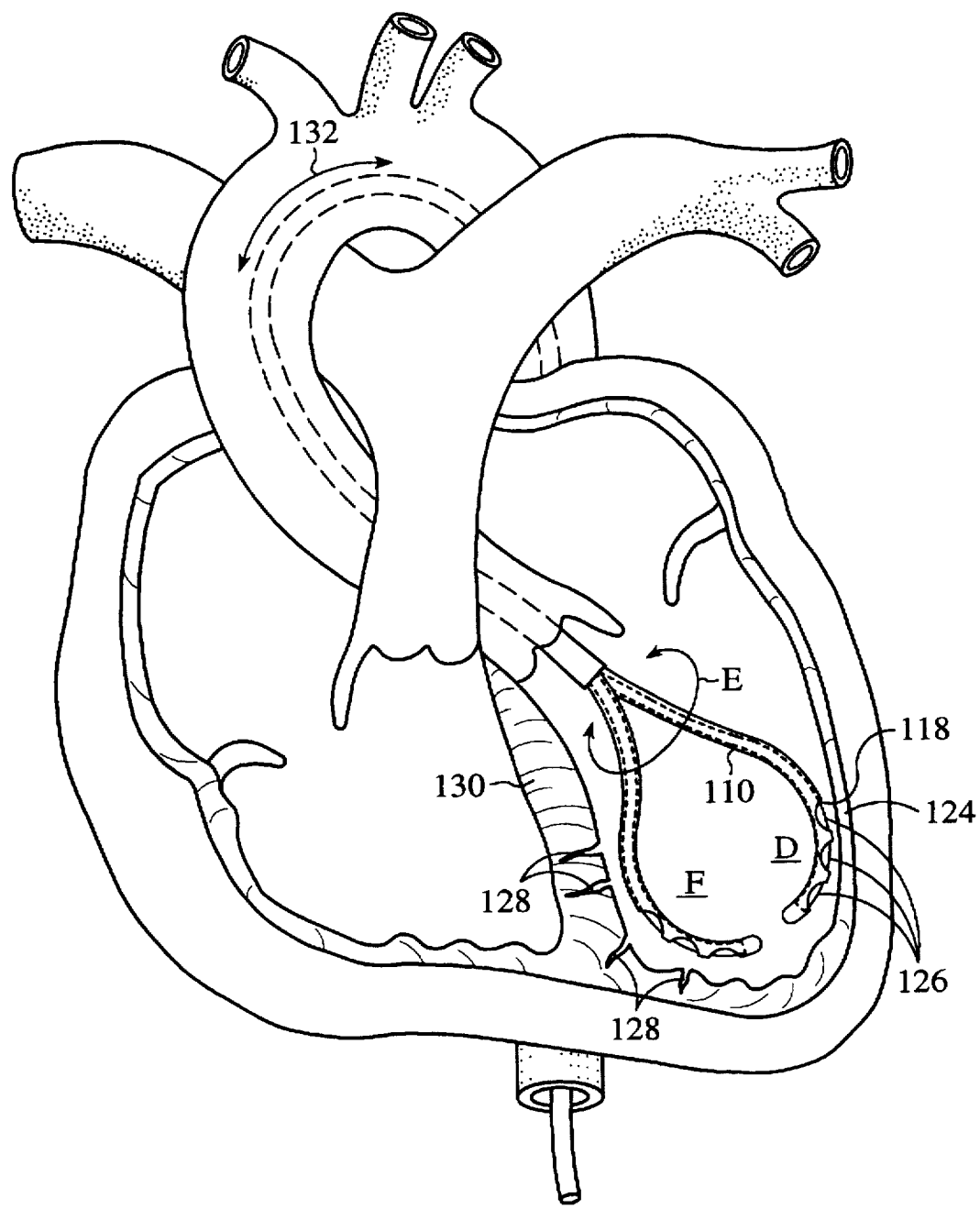
FIG. 5 is a representative perspective view of a preferred embodiment of the present invention positioned inside the left ventricle of the heart in a first position.

FIG. 5 is a representative perspective view of a preferred embodiment of the present invention positioned inside the left ventricle of the heart in a first position D. This position is adjacent a first surface area 124, in this case a portion of endocardium. In this position, the catheter can treat a series of individual preselected treatment points 126 of endocardium. Following treatment, the apparatus can be rotated in the direction shown by directional arrow E. This would result in placing the catheter in position F. An additional series of individual preselected treatment points 128 of a different surface area of endocardium 130 can be treated. It will be clear that the apparatus of the present invention can be rotated about its central axis 132 through a wide range of angular positions so as to treat a number of different surface areas during a given procedure.

Figure 6:
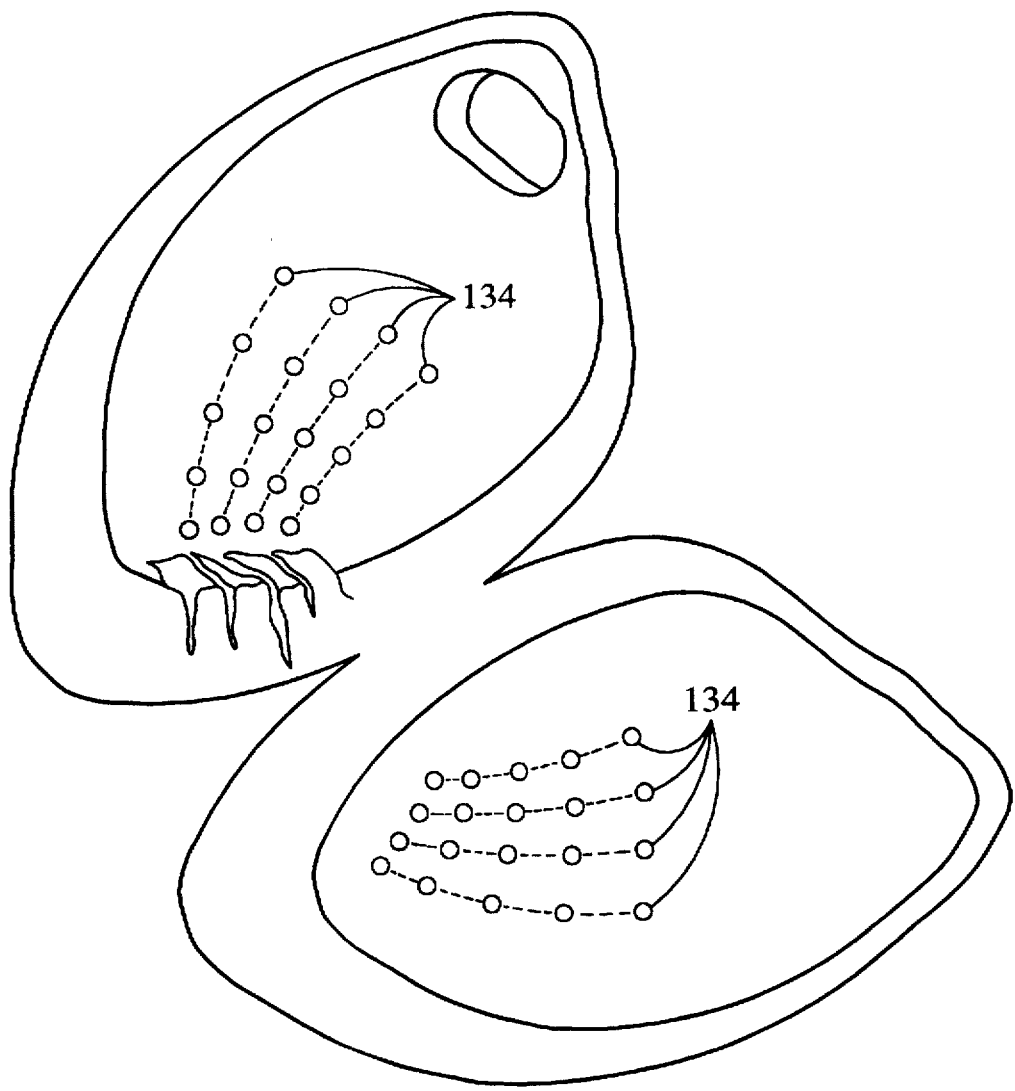
FIG. 6 is a representative perspective view of a treatment pattern made by a preferred embodiment of the present invention.

FIG. 6 is a representative perspective view of a treatment pattern made by a preferred embodiment of the present invention. This view is of the inside portion of the left ventricle. As described above in the case of TMR, a first set of individual TMR channels 134 in a single row can be created by alternatingly extending and retracting a laser delivery means through the inner sleeve and the guide holes of the outer sheath. Thereafter, by precisely controlled rotation of the apparatus about a central axis, as shown in the prior figure, additional rows or sets of individual TMR channels 134 can be created essentially parallel to the first set of individual TMR channels. Additional sets of TMR channels can be created to effectively cover a significant portion of interior heart wall, as desired, with TMR channels. It will be understood that essentially any desired number or density of TMR channels can be created in a given portion of the heart. Thermal energy accumulation as well as interconnection of adjacent channels are factors, among others, to be considered in such dense TMR channeling schemes.

One method of use of such an apparatus includes the preliminary steps of extending a laser delivery means such as an optical fiber or other laser delivery means through the inner sleeve, such that the distal end of the laser deliver means is adjacent the opening in the distal end of the inner sleeve, and also extending the inner sleeve through the outer sheath such that the opening at the distal end of the inner sleeve is operatively positioned adjacent a guide hole in the outer sheath. The sleeve and sheath assembly is inserted, in an elongated shape, optionally through an introducer sheath, guiding catheter, over a guide wire or in conjunction with other optional catheter equipment, through the vasculature of the patient or otherwise into the body opening, lumen or cavity.

Once inside, the shaped outer sheath will assume its operative shape and be firmly positionable against a curved wall structure in a first orientation. A laser delivery means can be extended through the opening at the distal end of the inner sleeve and be extended through the guide hole in the outer sheath adjacent the distal opening in the inner sleeve for treatment of the structure, body lumen, opening or otherwise, including a heart chamber wall. In the case of TMR, the laser delivery means could be an optical fiber or fiber bundle which would be extended through the catheter into an endocardial surface for the creation of channels into myocardium.

The fiber can also be used initially to pierce the endocardial surface. This will minimize bleeding from the endocardium. Then, advancing a fiber or other laser delivery means with a piercing tip a predetermined distance into the myocardium while simultaneously delivering laser energy will create a TMR channel or other treatment site. Alternatively, retro-lasing can then be performed. This novel method includes the steps of advancing a fiber or other laser delivery means with a piercing tip a predetermined distance into the myocardium and then delivering laser energy to create a TMR channel or other treatment site while retracting the fiber, laser delivery means or other functional device. Therefore, with regard to TMR, inasmuch as laser energy is only delivered during retraction of the fiber, the possibility of advancing the fiber too far and lasing through the epicardium is eliminated, as are complications arising from such epicardial perforations including but not limited to cardiac tamponade (a buildup in the pericardial sac of an excess of fluid such as blood), proliferation of adhesions, etc.

After creating the channel or otherwise effecting treatment, the distal end of the laser delivery means is retracted into the inner sleeve. Then the inner sleeve with the laser delivery means can be retracted in concert through the outer sheath such that the distal opening of the inner sleeve is adjacent and operatively aligned with a next guide hole. In a preferred embodiment, the inner sleeve will have a preformed resiliency thereby urging it into an operative position aligning the distal opening of the inner sleeve with one or more of the plurality of guide holes on the outer radial surface or elsewhere on the outer sheath. An optical fiber or other laser delivery means can be advanced sequentially through the guide holes of the outer sheath to treat a number of locations. Additionally, rotation of the catheter apparatus about its central axis will allow the apparatus to be repositioned such that it can be placed adjacent additional surfaces or structures for treatment thereon or therein.

Methods of performing TMR include the formation of sets of TMR channels from endocardial surfaces of the ventricle by alternatingly extending and retracting a laser delivery means such as an optical fiber or fiber bundle through each of the plurality of guide holes on the outer sheath. By holding the apparatus in a given orientation or position within the ventricle, each set of TMR channels into myocardium will be essentially perpendicular to each other and will initiate along an essentially straight line on an endocardial surface. Additional sets of TMR channels can be created by retracting the optical fiber or other laser delivery means inside the inner sleeve and rotating the outer sheath in unison with the inner sleeve and fiber, laser tool or other laser delivery means about the central axis of the apparatus into additional positions such that the shaped portion of the outer sheath is in contact with different portions of the wall or other surfaces within the heart. By repeating the sequence of slight rotation followed by creation of a TMR channel through each one of the guide holes on the outer sheath, an entire TMR procedure placing a large number of appropriately grouped and spaced TMR channels from one or more endocardial surfaces can be accomplished rapidly and uniformly.

The shape of the outer sheath is complementary to the shape of the interior heart wall surface, the guide holes on the inner sleeve will efficiently guide the laser delivery means into myocardium at preselected positions. Adaptation of a guide wire through the inner sleeve, outside of the inner sleeve or through a sidewall of the inner sleeve will enhance control.

Furthermore, adjunct use of appropriate drug delivery apparatus, blood seal means, depth stop apparatus such as clamps, etc., visualization means, marker means as well as other hardware and methodology will be considered within the scope of the present invention. Visualization can be enhanced with ultrasound or by using radio-opaque materials for construction, metal or other material foils or bands, especially at or adjacent distal ends of the outer jacket, the guide tube, and even on the optical fibers themselves. This will assist the practitioner in fluoroscopy or other visualization methodology for precise and accurate positioning of the apparatus.

The simple robust construction of the present invention will be apparent to those skilled in the art. Operation can be facilitated by employing a handle portion with an indexed rotating portion for rotating the assembly through a predetermined angular distance. The fibers or other laser delivery means pass through the handle and are attached to mechanisms for advancement and retraction therethrough. Additionally, the handle includes a guide hole selection indicator for informing the practitioner which guide hole along the length of the guide tube is being accessed by a laser delivery means. Additionally, indexed or other type depth-stop adjustment means for selecting the depth of fiber advance can be provided. Optionally, automatic fiber advance meals such as a thumbwheel-actuated fiber advance mechanism may be provided, as well as a guide, index or meter means for controlling or displaying the rotation of the guide tube within the outer jacket. Such fiber advance means, depth stop adjust means, rotation control means as well as other auxiliary control mechanisms are more fully described in co-pending U.S. patent applications Ser. No. 08/675,698 and Ser. No. 08/675,732, allowed both filed Jul. 3, 1996, as well as Ser. No. 08/664,956 filed on Jun. 13, 1996.

A preferred embodiment of the method for performing a medical procedure involving delivery of laser energy for TMR, stimulation, etc., will be understood by the foregoing as well as the following. With regard to a preferred embodiment of the apparatus of the present invention, a guiding catheter, optionally the outer sheath of the apparatus of the present invention or alternatively a separate tube which enters the vasculature percutaneously or otherwise. A guide wire can also be placed inside the initial guiding catheter to be attached to a distal point within the ventricle or elsewhere. Once attached, the guiding catheter can be withdrawn and the apparatus of the present invention placed within the ventricle utilizing the guide wire installed. The use of a guide wire in conjunction with the methods and apparatus of the present invention for steering the apparatus through the vasculature and into preselected portions of the ventricle is contemplated and included within the scope of this invention. Such guide wires and other tether means are more fully described in co-pending U.S. patent application Ser. No. 08/627,704 allowed filed Mar. 29, 1996.

A preferred embodiment of the method for performing a medical procedure involving delivery of laser energy for TMR, stimulation, etc., will be understood by the foregoing as well as the following. A guiding catheter, optionally the outer sheath of the apparatus of the present invention or alternatively a separate tube, is placed into the vasculature percutaneously or otherwise. The apparatus of the present invention is then introduced to the vasculature through this guiding catheter. A guide wire can also be placed inside the initial guiding catheter to be attached to a distal point within the ventricle or elsewhere. Once attached, the guiding catheter can be withdrawn and the apparatus of the present invention placed within the ventricle utilizing the guide wire installed. The use of a guide wire in conjunction with the methods and apparatus of the present invention for steering the apparatus through the vasculature and into preselected portions of the ventricle is contemplated and included within the scope of this invention. Such guide wires and other tether means are more fully described in co-pending U.S. patent application Ser. No. 08/627,704 filed Mar. 29, 1996.

The present invention is intended for use with any medical laser. In particular, the Holmium or excimer laser is particularly suited to the present invention. However, any suitable laser source, pulsed or otherwise, could provide laser energy to the laser delivery means of the present invention for performing the method of the present invention. Likewise, the catheter and surgical equipment, including laser delivery means, referred to in the present document as well as that known and used in medicine and other disciplines today and in the future, will be included in the scope of this disclosure. Such laser delivery means include, but are not limited to, individual optical fibers as well as bundles of fibers with and without piercing tips and with or without firing tips or fiber ends having shaped or contoured end faces for selectively diverging the laser beam or other laser energy diverging means, rods, mirrors configurations and other laser delivery means with and without focusing lens and the like. It will also be understood that the apparatus and method of the present invention as described herein, including the novel combination or use with of any conventional mechanism or method which are known to those skilled in the art, are included within the scope of this invention.

It will further be understood that while the present invention has been described for performing TMR on endocardial surfaces in the left ventricle, the apparatus and methods described herein are equally intended for use in any suitable procedure, including but not limited to procedures where any device need be extended through a guiding catheter to an opening or other point within the body for other medical procedures including laser treatment, visualization, biopsy, etc. "Stimulation", for example, is performed by using laser energy to create zones or pockets, optionally interconnected at least initially by small channels ablated through the tissue, for the introduction of blood born growth and healing factors and stimulated capillary growth surrounding the lased zones or pockets to create an increased supply of oxygen to the tissue and thus a revitalization of the heart muscle. Methods and apparatus for causing stimulation are more fully described in co-pending U.S. patent application Ser. No. 08/664,956 filed Jun. 13, 1996.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

I claim:

1. A catheter device, the device comprising:
   treatment means for performing interventional procedures in the body consisting essentially of a treatment device;

an outer flexible tubular sheath having proximal and distal ends and a side-wall having at least one portal for positioning the treatment device at predetermined body surfaces;

a tubular inner sleeve that is slidably disposed within the outer sheath, has a proximal end and a distal end, has a guide opening at the inner sleeve's distal end and encompasses the treatment device which is slidably extendable through the guide opening; and the inner sleeve's guide opening is configured substantially to be coextensive with the at least one portal when slidably positioned and aligned therewith forming a communicating channel for the treatment device to egress from the outer sheath, and the treatment device, outer tubular sleeve and the inner sleeve are not co-axially aligned at the communicating channel from which the treatment device can egress.

2. The catheter device of claim 1 wherein the at least one portal is a plurality of portals.

3. The catheter device of claim 2 wherein the portals on the outer sheath are located along the distal length of the outer sheath.

4. The catheter device of claim 1 wherein the outer sheath is torquable and curvilinear shaped.

5. The catheter device of claim 4 wherein the outer sheath's distal section is essentially j-shaped.

6. The catheter device of claim 1 wherein at least a portion of the outer sheath is constructed from shape memory alloy.

7. The catheter device of claim 1 wherein side-walls of the inner sleeve and the outer sheath each have a complementary conformal cross-sectional geometry that is non-circular thereby preventing rotation of the inner sleeve within the outer sheath.

8. The device of claim 7 wherein the each of the side-walls of the inner sleeve and the outer sheath are tear-drop shaped.

9. The catheter device of claim 1 wherein side-walls of the inner sleeve the outer sheath each have a complementary conformal cross-sectional geometry that is substantially circular thereby allowing rotatability of the inner sleeve within the outer sheath.

10. The catheter device of claim 1 wherein the distal end of the inner sleeve's lumen has a transitional smooth-curvature cam member that aligns with the at least one portal, thereby allowing deflectability and movability of the treatment device through the at least one portal.

11. The catheter device of claim 1 wherein the treatment device is a laser energy delivery means for irradiating tissue.

12. The catheter device of claim 11 wherein the laser energy delivery means' distal end includes at least one optical fiber.

13. The catheter device of claim 11 wherein the laser energy delivery means' distal end includes a focusing device.

14. A method of performing an interventional procedure in a body, the method comprising the steps of:

a) providing a catheter device that includes:

a treatment means for performing the interventional procedure in the body consisting essentially of a treatment device;

an outer flexible tubular sheath having proximal and distal ends and a side-wall having at least one portal for positioning the treatment device at predetermined body surfaces;

a tubular inner sleeve that is slidably disposed within the outer sheath, has a proximal end and a distal end, has a guide opening at the inner sleeve's distal end and encompasses the treatment device which is slidably extendable through the guide opening; and the inner sleeve's guide opening is configured substantially to be coextensive with the at least one portal when slidably positioned and aligned therewith forming a communicating channel for the treatment device to egress from the outer sheath, and the treatment device, outer tubular sleeve and the inner sleeve are not co-axially aligned at the communicating channel from which the treatment device can egress;

b) positioning the distal end of the outer sheath in the body;

c) aligning the inner sleeve's guide opening with the outer sheath's at least one portal;

d) moving the treatment device through the guide opening and the at least one portal; and e) performing the interventional procedure at the predetermined body surfaces.

15. The method of claim 14 wherein during the step b), the catheter device temporarily has an elongated shape.

16. The method of claim 14 further including prior to step b) a step of positioning a guide wire to facilitate positioning of the outer sheath's distal end.

17. The method of claim 14 further including in the catheter device that has a plurality of portals the following steps after step e) of:

f) retracting the treatment device into the inner sleeve;

g) re-positioning the guide opening adjacent a subsequent portal;

h) extending the treatment device through the guide opening and the subsequent portal; and i) performing the interventional procedure at a subsequent location.

18. The method of claim 14 further including in the catheter device that has a plurality of portals the following steps after step e) of:

f) retracting the treatment device into the inner sleeve;

g) rotating the guiding catheter device within the body h) re-positioning the guide opening adjacent a subsequent portal;

i) extending the treatment device through the guide opening and the subsequent portal; and j) performing the interventional procedure at a subsequent location.

19. The method of claim 14 wherein the predetermined location is on an endocardial surface in a left ventricle of the heart.

20. The method of claim 19 wherein the treatment is myocardial revascularization for creating channels.

21. The method of claim 20 wherein the treatment device is a laser energy delivery device and the treatment step e) includes steps for: i) advancing the laser energy delivery device through the endocardial surface into myocardium tissue and ii) delivering laser energy to effectuate tissue ablation.

22. The method of claim 21 wherein further including prior to the step e) a step for piercing the endocardium prior to advancing the laser energy delivery device.

23. The method of claim 22 wherein after the step for piercing and advancing the laser energy device, the delivery of the laser energy occurs during a step of retracting the laser energy device from myocardium tissue.

24. A catheter device for performing interventional cardiological procedures, the device comprising:

treating means for performing the interventional cardiological procedures consisting essentially of a treatment device;

guiding means for guiding the treating means to predetermined locations within the heart's ventricle; and location selecting means for selectively guiding the treating means to the predetermined locations and allowing the treating means to egress from the guiding means, the location selecting means telescopically encompasses the treating means, and the guiding means telescopically encompasses the location selecting means, the location selecting means is repositionable within the guiding means, whereby selectively aligning the guiding means with the location selecting means enables positioning of the treating means at any of the predetermined locations.

\* \* \* \* \*